United States Patent [19]
Lukacovic et al.

[11] Patent Number: 5,885,556
[45] Date of Patent: Mar. 23, 1999

[54] TARTAR CONTROL ORAL COMPOSITIONS

[75] Inventors: Michael Frederick Lukacovic, West Chester; Liezl Gonzales Peterson, Loveland; Steven Carl Burgess, Sharonville; Gregory Berry, Cincinnati; Mary Ann Hunter-Rinderle, Mason, all of Ohio

[73] Assignee: The Procter & Gamble Company, Cincinnati, Ohio

[21] Appl. No.: 695,350

[22] Filed: Aug. 6, 1996

Related U.S. Application Data

[63] Continuation-in-part of Ser. No. 584,832, Jan. 11, 1996, abandoned.

[51] Int. Cl.$^6$ ............................................. A61K 7/16
[52] U.S. Cl. ............................................. 424/57; 424/49
[58] Field of Search .................................. 424/49–58

[56] References Cited

U.S. PATENT DOCUMENTS

| | | | |
|---|---|---|---|
| 4,144,322 | 3/1979 | Cordon et al. | 424/49 |
| 4,487,757 | 12/1984 | Kiozpeoplou | 424/7.1 |
| 4,515,772 | 5/1985 | Parran, Jr. et al. | 424/57 |
| 4,623,536 | 11/1986 | Winston et al. | 424/49 |
| 4,684,518 | 8/1987 | Parran, Jr. et al. | 424/52 |
| 4,687,663 | 8/1987 | Schaeffer | 424/52 |
| 4,721,614 | 1/1988 | Winston et al. | 424/52 |
| 4,806,339 | 2/1989 | Parran, Jr. et al. | 424/52 |
| 4,806,340 | 2/1989 | Gaffar et al. | 424/52 |
| 4,822,599 | 4/1989 | Mitra | 424/52 |
| 4,885,155 | 12/1989 | Parran, Jr. et al. | 424/52 |
| 4,906,456 | 3/1990 | Gaffar et al. | 424/52 |
| 4,966,777 | 10/1990 | Gaffar et al. | 424/52 |
| 4,983,379 | 1/1991 | Schaeffer | 424/52 |
| 4,999,184 | 3/1991 | Parran, Jr. et al. | 424/52 |
| 5,059,417 | 10/1991 | Williams et al. | 424/53 |
| 5,180,576 | 1/1993 | Winston et al. | 424/52 |
| 5,186,926 | 2/1993 | Williams et al. | 424/53 |
| 5,215,740 | 6/1993 | Domke et al. | 424/52 |
| 5,256,402 | 10/1993 | Prencipe et al. | 424/53 |
| 5,292,502 | 3/1994 | Burke et al. | 424/54 |
| 5,296,215 | 3/1994 | Burke et al. | 424/49 |
| 5,372,803 | 12/1994 | Williams et al. | 424/53 |
| 5,424,059 | 6/1995 | Prencipe et al. | 424/52 |
| 5,456,903 | 10/1995 | Huetter et al. | 424/57 |
| 5,496,541 | 3/1996 | Cutler | 424/50 |
| 5,565,190 | 10/1996 | Santalucia et al. | 424/53 |
| 5,630,999 | 5/1997 | Burke et al. | 424/49 |

FOREIGN PATENT DOCUMENTS

| | | | |
|---|---|---|---|
| 0725118 B1 | 8/1996 | European Pat. Off. | C09K 3/14 |
| 2079325 | 1/1996 | Spain | A61K 7/28 |

OTHER PUBLICATIONS

08/365,975, Huetter et al., Dec. 28, 1994.

*Primary Examiner*—Shep K. Rose
*Attorney, Agent, or Firm*—Angela Marie Stone; Betty J. Zea

[57] ABSTRACT

Disclosed are oral compositions comprising a nonionic surfactant and/or amphoteric surfactant, an anionic surfactant, free pyrophosphate ions or tetrasodium pyrophosphate, free fluoride ions, and one or more aqueous carriers. The compositions may also contain an alkali metal bicarbonate salt and xylitol.

2 Claims, No Drawings

TARTAR CONTROL ORAL COMPOSITIONS

This is a continuation-in-part of application Ser. No. 08/584,832, filed on Jan. 11, 1996 now abandoned.

BACKGROUND OF THE INVENTION

Dental calculus, or tartar as it is sometimes called, is a deposit which forms on the surface of the teeth at the gingival margin. Supraginival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel, and dentine. An organic portion is also present and consists of desquamated epithelial cells, leukocytes, salivary sediment, food debris, and various types of microorganisms.

As the mature calculus develops, it becomes visibly white or yellowish in color unless stained or discolored by some extraneous agent. This is undesirable from an aesthetic standpoint.

Mechanical removal of calculus periodically by the dentist is routine dental office procedure. A variety of chemical and biological agents have also been suggested to retard calculus formation or to remove calculus after it is formed. Pyrophosphate salts are chemical agents known to have the ability to retard calculus formation as described, for example, in U.S. Pat. No. 4,999,184, to Parran, Jr. et al., issued Mar. 12, 1991, the disclosure of which is incorporated herein by reference in its entirety.

Agents used to retard the growth of tartar may cause increased oral desquamation levels. To keep the desquamation levels at an acceptable level, the amount of surfactant or amount of surfactant and tartar control agent is lowered. The lowering of the amount of surfactant results in decreased foam levels, which commonly causes negative aesthetics due to the lower foam levels experienced during brushing.

It has been discovered by the present inventors that oral tartar control compositions can be formulated with a combination of surfactants which increase consumer acceptance by increasing foaming levels while maintaining acceptable oral desquamation levels. It has also been discovered that these compositions can also contain an alkali metal bicarbonate salt and xylitol, while maintaining the improved level of foaming.

It is therefore an object of the present invention to provide a tartar control composition which contains a combination of surfactants. It is also an object of the present invention to provide a consumer acceptable tartar control composition which does not increase oral desquamation levels.

These and other objects of the present invention will become readily apparent from the detailed description which follows.

All percentages and ratios used are by weight of the total composition, and all measurements are made at 25° C., unless otherwise specified.

SUMMARY OF THE INVENTION

The present invention relates to an oral composition comprising from about 0.025% to about 5% of a surfactant selected from the group consisting of nonionic surfactants, amphoteric surfactants, and combinations thereof, from about 0.025% to about 9% of an anionic surfactant, an amount of at least about 1.5% tetrasodium pyrophosphate, from about 50 ppm to about 3500 ppm of free fluoride ions, and from about 85% to about 99% of one or more aqueous carriers. The invention may also include from about 0.5% to about 30% of an alkali metal bicarbonate salt and from about 2% to about 25% of xylitol.

The present invention also relates to an oral composition comprising from about 0.025% to about 5% of a surfactant selected from the group consisting of nonionic surfactants, amphoteric surfactants, and combinations thereof, from about 0.025% to about 9% of an anionic surfactant, an amount of at least one dissolved pyrophosphate ion source sufficient to provide at least about 1.0% free pyrophosphate ions, from about 50 ppm to about 3500 ppm of free fluoride ions, and from about 40% to about 97% of one or more aqueous carriers. The invention may also include from about 0.5% to about 30% of an alkali metal bicarbonate salt and from about 2% to about 25% of xylitol.

DETAILED DESCRIPTION OF THE INVENTION

The present invention relates to oral compositions comprising a combination of surfactants, specifically a nonionic and/or amphoteric surfactant and an anionic surfactant. These compositions can also include an alkali metal bicarbonate salt and xylitol.

The oral compositions of the present invention may be in the form of a toothpaste, mouth rinse, and liquid dentifrice. The term "toothpaste", as used herein, means paste, powder, or gel formulations unless otherwise specified.

The term "oral composition" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

The term "aqueous carrier" as used herein means any safe and effective materials for use in the compositions of the present invention. Such materials include thickening materials, humectants, water, buffering agents, abrasive polishing materials, titanium dioxide, flavoring agents, sweetening agents, coloring agents, and mixtures thereof.

The present compositions comprise several essential components, as well as optional components. The essential and optional components of the compositions of the present invention are described in the following paragraphs.

Surfactants

The present compositions comprise surfactants, also commonly referred to as sudsing agents. Suitable surfactants are those which are reasonably stable and foam throughout a wide pH range. Many of these suitable nonionic and amphoteric surfactants are disclosed by Gieske et al., U.S. Pat. No. 4,051,234, issued Sep. 27, 1977, and many suitable nonionic surfactants are disclosed by Agricola et al., U.S. Pat. No. 3,959,458, issued May 25, 1976, both incorporated herein in their entirety by reference.

a). Nonionic and Amphoteric Surfactants

Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials.

The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed.

The present composition typically comprises a nonionic, amphoteric, or combination of nonionic and amphoteric surfactant each at a level of from about 0.025% to about 5%, preferably from about 0.05% to about 4%, and most preferably from about 0.1% to about 3%.

b). Anionic Surfactants

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. The present composition typically comprises an anionic surfactant at a level of from about 0.025% to about 9%, preferably from about 0.05% to about 7%, and most preferably from about 0.1% to about 5%.

Pyrophosphate Source

The present invention also includes a pyrophosphate ion source which is from a pyrophosphate salt. The pyrophosphate salts useful in the present compositions include the dialkali metal pyrophosphate salts, tetra alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%. Free pyrophosphate ions may be present in a variety of protonated states depending on a the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aestetically acceptable and readily soluble during use. The amount of pyrophosphate salt useful in making these compositions is any tartar control effective amount, and is generally from about 1.5% to about 15%, preferably from about 2% to about 10%, and most preferably from about 3% to about 8%, by weight of the dentifrice composition. Some or all of the tetrasodium pyrophosphate is undissolved in the product and is present as tetrasodium pyrophosphate particles. Pyrophosphate ions in different protonated states (e.g., $HP_2O_7^{-3}$) may also exist depending upon the pH of the composition.

Compositions may also comprise a mixture of dissolved and undissolved pyrophosphate salts. Any of the above mentioned pyrophosphate salts may be used.

The pyrophosphate salts are described in more detail in Kirk & Othmer, *Encyclopedia of Chemical Technology*, Third Edition, Volume 17, Wiley-Interscience Publishers (1982), incorporated herein by reference in its entirety, including all references incorporated into Kirk & Othmer.

Optional agents to be used in place of or in combination with the pyrophosphate salt include such known materials as synthetic anionic polymers [including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as e.g., polyamino propoane sulfonic acid (AMPS)], zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

Free Fluoride Ions

The present invention may also incorporate free fluoride ions. Preferred free fluoride ions can be provided by sodium fluoride, stannous fluoride, indium fluoride, and sodium monofluorophosphate. Sodium fluoride is the most preferred free fluoride ion. Norris et al., U.S. Pat. No. 2,946,725, issued Jul. 26, 1960, and Widder et al., U.S. Pat. No. 3,678,154 issued Jul. 18, 1972, disclose such salts as well as others. Both patents are incorporated herein by reference in their entirety.

The present composition may contain from about 50 ppm to about 3500 ppm, and preferably from about 500 ppm to about 3000 ppm of free fluoride ions.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 30%, preferably from about 0.5% to about 15%, and most preferably from about 0.5% to about 5% of an alkali metal bicarbonate salt.

Xylitol

The present invention may also include xylitol. Xylitol is a sugar alcohol that is used as a sweetener and humectant. Xylitol may provide a therapeutic effect, such as an antibacterial or anticaries effect. The present compositions typically comprise xylitol at a level from about 2% to about 25%, preferably from about 3% to about 15%, and most preferably from about 5% to about 12%.

Aqueous Carriers

In preparing the present compositions, it is desirable to add one or more aqueous carriers to the compositions. Such materials are well known in the art and are readily chosen by one skilled in the art based on the physical and aesthetic properties desired for the compositions being prepared. Aqueous carriers typically comprise from about 45% to about 99%, and preferably from about 70% to about 95%.

The present invention compositions in the form of toothpastes, typically contain some thickening material or binders to provide a desirable consistency. Preferred thickening agents are carboxyvinyl polymers, carrageenan, hydroxyethyl cellulose, and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an amount from about 0.1% to about 15%, by weight of the total composition.

Another optional component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, and other edible polyhydric alcohols. The humectant generally comprises from about 0% to 70%, and preferably from about 15% to 55%, by weight of the compositions herein.

Water employed in the preparation of commercially suitable oral compositions should preferably be of low ion content and free of organic impurities. Water generally comprises from about 5% to about 70%, and preferably from about 20% to about 50%, by weight of the composition herein. These amounts of water include the free water which is added plus that which is introduced with other materials, such as with sorbitol.

The pH of the present compositions is preferably adjusted through the use of buffering agents. Buffering agents, as used herein, refer to agents that can be used to adjust the pH of the compositions to a range of about pH 6.5 to about pH 10. These agents include monosodium phosphate, trisodium phosphate, sodium hydroxide, sodium carbonate, citric acid, and sodium citrate. Buffering agents can be used at a level of from about 0.5% to about 10%, by weight of the present compositions.

An abrasive polishing material may also be included in the toothpaste compositions. The abrasive polishing material contemplated for use in the compositions of the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al in U.S. Pat. No. 3,070,510, issued Dec. 25, 1962, incorporated herein by reference. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Preferred are the silica xerogels marketed under the trade name "Syloid" by the W.R. Grace & Company, Davison Chemical Division. Also preferred are the precipitated silica materials such as those marketed by the J.M. Huber Corporation under the trade name, "Zeodent", particularly the silica carrying the designation "Zeodent 119". The types of silica dental abrasives useful in the toothpastes of the present invention are described in more detail in Wason, U.S. Pat. No. 4,340,583, issued Jul. 29, 1982, incorporated herein by reference. The abrasive in the toothpaste compositions described herein is generally present at a level of from about 6& to about 70% by weight of the composition. Preferably, toothpastes contain from about 10% to about 50% of abrasive, by weight of the composition.

Titanium dioxide may also be added to the present composition. Titanium dioxide is a white powder which adds opacity to the compositions. Titanium dioxide generally comprises from about 0.25% to about 5% by weight of the compositions.

Flavoring agents can also be added to the compositions. Suitable flavoring agents include oil of wintergreen, oil of peppermint, oil of spearmint, oil of sassafras, clove bud oil, menthol, anethole, methyl salicylate, eucalyptol, cassia, l-methol acetate, sage, eugenol, parsley oil, oxanone, alpha-irisone, marjoram, lemon, orange, propenyl guaethol, cinnamon, and mixtures thereof. Flavoring agents are generally used in the compositions at levels of from about 0.001% to about 5%, by weight of the composition.

Sweetening agents can be added to the compositions. These include saccharin, dextrose, sucrose, lactose, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from about 0.005% to about 5%, by weight of the composition.

The present invention may also include other agents. Included among such agents are water insoluble non-cationic agents such as triclosan and other agents of the type disclosed in Parran, Jr. et al., U.S. Pat. No. 5,015,466, issued May 14, 1991, incorporated by reference herein in its entirety.

The present compositions can be in the form of a mouth rinse or liquid dentifrice where conventional mouth rinse components comprise the aqueous carriers of the present invention. Mouth rinses and liquid dentifrices generally comprise from about 20:1 to about 2:1 of a water ethyl alcohol or alcohol free solution, and preferably other ingredients such as flavors, sweeteners, and humectants as those mentioned above. The humectants, such as glycerin and sorbitol, give a moist feel to the mouth. Generally on a weight basis, the mouth rinses and liquid dentifrices of the present invention comprise from about 0% to about 60% ethyl alcohol, from about 0% to about 20% humectant, from about 0% to about 0.5% sweetening agent, from about 0% to about 0.3% flavoring agent, and the balance water. Other optional components described herein for use in toothpaste products are also useful in the mouth rinse and liquid dentifrice compositions.

Method of Manufacturing

Toothpaste compositions of the present invention are prepared by mixing together the components described above. If the present composition contains predominately dissolved pyrophosphate salt, the method of manufacturing comprises conventional toothpaste manufacturing methods. A typical method is described after Example 1.

If the present composition contains predominately undissolved pyrophosphate salt, the method of manufacturing comprises the steps of: (a) preparing a mixture of a surfactant selected from the group consisting of nonionic surfactants, amphoteric surfactants, and combinations thereof, an anionic surfactant, free fluoride ions, an alkali metal bicarbonate salt, and one or more aqueous carrier materials; (b) adding tetrasodium pyrophosphate, all at once or in portions, under conditions whereby less than about 20% of the total pyrophosphate is dissolved in the dentifrice mixture; and wherein further any remaining aqueous carrier materials not added to the mixture during step (a) are added in whole or in part in step (b) or thereafter, either by themselves or with any remaining amount of the tetrasodium pyrophosphate, under conditions such that less than about 20% of the total pyrophosphate is dissolved in the mixture. Preferably, the amount of pyrophosphate dissolved in the mixture for the methods and compositions of the present invention is less than about 10% by weight of the total pyrophosphate present in the compositions. Preferably, one or more of the following process conditions are controlled as follows to limit the solubility of the tetrasodium pyrophosphate in the dentifrice mixture: (1) the neat (undiluted) pH of the process mixture is above about pH 8 during and after the tetrasodium pyrophosphate is added to the mixture; (2) the tetrasodium pyrophosphate salt is one of the last components to be added to the process mixture, preferably after all or much of the other sodium-containing salts present in the composition have been added to the process mixture; and (3) during and after the tetrasodium pyrophosphate salt is added, the temperature of the mixture is not greater than about 60° C., and preferably during addition is less than about 38° C. By this method, the composition will have less than about 20% of the total pyrophosphate dissolved in the dentifrice composition and the dissolved tetrasodium pyrophosphate salt is less likely to recrystalize in the form of glass-like crystal particles of tetrasodium pyrophosphate decahydrate.

Method of Treatment

The present invention compositions additionally relate to a method for reducing the incidence of calculus on dental enamel. The method of treatment herein comprises contacting the dental enamel surfaces in the mouth with the oral compositions according to the present invention.

The following examples further describe and demonstrate embodiments within the scope of the present invention. These examples are given solely for the purpose of illustration and are not to be construed as limitations of the present invention as many variations thereof are possible without departing from the spirit and scope.

| Ingredient | Weight % |
|---|---|
| Sorbitol[a] | 22.500 |
| Xylitol | 10.000 |
| Water | 20.284 |
| Saccharin | 0.400 |
| Sodium Fluoride | 0.243 |
| Glycerin | 7.000 |
| Carboxymethylcellulose | 0.700 |
| Polyethylene Glycol | 3.000 |
| Tetrasodium Pyrophosphate | 0.783 |
| Sodium Acid Pyrophosphate | 3.157 |
| Tetrapotassium Pyrophosphate[b] | 6.283 |
| Silica | 20.000 |
| Sodium Alkyl Sulfate[c] | 4.000 |
| Poloxamer 407 | 0.250 |
| Color | 0.300 |
| Flavor | 1.100 |

Example 1 is prepared as follows. Start by combining water and sorbitol. Add xylitol and poloxamer to the mixture. Mix thoroughly and add sodium fluoride and saccharin. In the order listed, add sodium acid pyrophosphate, tetrasodium pyrophosphate, and tetrapotassium pyrophosphate. Next add the silica. Disperse the carboxymethylcellulose in the remaining humectants, polyethylene glycol and glycerin, before adding to the mixture. Lastly, add the flavor, coloring agents, and remaining surfactant, sodium alkyl sulfate. Continue mixing until homogeneous. Mill and/or deareate the final product if desired for aesthetic preference.

| Ingredient | Weight % |
|---|---|
| Sorbitol[a] | 33.000 |
| Water | 10.311 |
| Saccharin | 0.300 |
| Sodium Fluoride | 0.243 |
| Glycerin | 10.000 |
| Propylene Glycol | 5.000 |
| Polyethylene Glycol | 3.000 |
| Carboxymethylcellulose | 0.700 |
| Sodium Bicarbonate | 1.500 |
| Sodium Carbonate | 0.800 |
| Tetrasodium Pyrophosphate | 5.046 |
| Silica | 22.000 |
| Titanium Dioxide | 0.600 |
| Sodium Alkyl Sulfate[c] | 6.000 |
| Poloxamer 407 | 0.250 |
| Cocamidopropyl betaine | 0.250 |
| Flavor | 1.000 |

| Ingredient | Weight % |
|---|---|
| Sorbitol[a] | 21.500 |
| Water | 19.811 |
| Saccharin | 0.500 |
| Sodium Fluoride | 0.243 |
| Glycerin | 10.000 |
| Polyethylene Glycol | 1.000 |
| Carboxymethylcellulose | 1.000 |
| Sodium Bicarbonate | 20.000 |
| Sodium Carbonate | 1.250 |
| Tetrasodium Pyrophosphate | 5.046 |
| Silica | 15.000 |
| Color | 0.250 |
| Sodium Alkyl Sulfate[c] | 2.000 |
| Sodium Lauroyl Sarcosinate | 0.500 |
| Cocamidopropyl betaine | 1.000 |
| Flavor | 0.900 |

Examples II and III are prepared as follows. Start by combining water and sorbitol. If used, add propylene glycol and poloxamer to the mixtures. Mix thoroughly and add sodium fluoride and saccharin. Add sodium carbonate. Next add the silica. The temperature of the mixture should be about 32° C. or less prior to the addition of sodium bicarbonate. Next, disperse the thickening agent, carboxymethylcellulose, in the remaining humectants, polyethylene glycol and glycerin, before adding to the mixtures. Next add the flavor, coloring agents, titanium dioxide, and remaining surfactants, sodium alkyl sulfate and cocamidopropyl betaine, and if used, sodium lauroyl sarcosinate. Lastly, slowly add the tetrasodium pyrophosphate. Continue mixing until homogeneous. Mill and/or deareate the final product if desired for aesthetic preference.

| Ingredient | Weight % |
|---|---|
| Xylitol | 5.000 |
| Water | 26.500 |
| Saccharin | 0.400 |
| Sodium Fluoride | 0.243 |
| Glycerin | 23.561 |
| Polyethylene Glycol | 1.000 |
| Carboxymethylcellulose | 0.250 |
| Xanthan Gum | 0.600 |
| Sodium Bicarbonate | 2.500 |
| Sodium Carbonate | 1.250 |
| Tetrasodium pyrophosphate | 5.046 |
| Silica | 25.000 |
| Titanium Dioxide | 0.750 |
| Sodium alkyl sulfate[c] | 5.000 |
| Poloxamer 407 | 2.000 |
| Flavor | 0.900 |

(a) 70% solution of sorbitol in water
(b) 60% solution of tetrapotassium pyrophosphate in water
(c) 27.9% solution of sodium alkyl sulfate in water Example IV is prepared as follows. Start by combining water and enough glycerin to provide sufficient liquid for adequate mixing. Add xylitol and poloxamer to the mixture. Mix thoroughly and add sodium fluoride and saccharin. Add sodium carbonate. Next add the silica. The temperature of the mixture should be about 32° C. or less prior to the addition of sodium bicarbonate. Next, disperse the thickening agents, carboxymethylcellulose and xanthan gum, in the humectant, polyethylene glycol and remaining glycerin, before adding to the mixtures. Next add the flavor, titanium dioxide, and remaining surfactant, sodium alkyl sulfate. Lastly, slowly add the tetrasodium pyrophosphate. Continue mixing until homogeneous. Mill and/or deareate the final product if desired for aesthetic preference.

What is claimed is:

1. A method of manufacturing a bicarbonate salt tartar control dentifrice composition; said method comprising the steps of:

(a) preparing at a temperature at about 32° C. or less a mixture of a mixture of from about 0.025% to about 5.0% of a surfactant selected from the group consisting of nonionic surfactants selected from the group consisting of poloxamers, polyoxyethylene sorbitan esters, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials, amphoteric surfactants, and combinations thereof, from about 0.025% to about 9.0% of an anionic surfactants, fluoride ions, bicarbonate salt, and one or more aqueous carrier materials;

(b) adding tetrasodium pyrophosphate, all at once or in portions, under conditions whereby less than about 20% of the total pyrophosphate is dissolved in the dentifrice mixture which is at a temperature of less than about 38° C; and wherein any further remaining dentifrice carrier materials not added to the mixture during step (a) are added in whole or in part in step (b) or thereafter, either by themselves or with any remaining amount of the tetrasodium pyrophosphate under conditions such that less than about 20% of the total pyrophosphate is dissolved in the mixture;

said dentifrice composition manufactured by this process comprising from about 0.025% to about 5.0% of a surfactant selected from the group consisting of nonionic surfactants, amphoteric surfactants, and combinations thereof, from about 0.025% to about 9.0% of an anionic surfactant, from about 50 ppm to about 3500 ppm of free fluoride ions, from about 0.5% to about 20% a bicarbonate salt, from about 40% to about 97% of one or more aqueous carriers, and at least about 1.5% tetrasodium pyrophosphate, with said composition having less than about 20% of the total pyrophosphate dissolved in the dentifrice composition, wherein said composition containing dissolved tetrasodium pyrophosphate salt being less likely to recrystalize in the form of glass-like crystal particles of tetrasodium pyrophosphate decahydrate and wherein said surfactant selected from the group consisting of nonionic surfactants, amphoteric surfactants, and combinations thereof combined with said anionic surfactant does not increase oral desquamation levels, but does maintain an acceptable level of foaming during brushing.

2. The method of manufacturing a composition according to claim 1 wherein the tetrasodium pyrophosphate is added to the mixture after all other sodium-containing salts present in the composition have been added to the mixture.

* * * * *

UNITED STATES PATENT AND TRADEMARK OFFICE
CERTIFICATE OF CORRECTION

PATENT NO. : 5,885,556
DATED : March 23, 1999
INVENTOR(S) : Michael Frederick Lukacovic et al.

It is certified that error appears in the above-identified patent and that said Letters Patent is hereby corrected as shown below:

Column 1,
Line 9, "Supraginival" should read -- Supragingival --
Line 59, after the word "used", the word -- herein -- should be inserted.

Column 6,
Line 21, "6&" should read -- 6% --

Signed and Sealed this

Twelfth Day of August, 2003

JAMES E. ROGAN
*Director of the United States Patent and Trademark Office*